United States Patent [19]

Seefeldt et al.

[11] Patent Number: 5,708,190
[45] Date of Patent: Jan. 13, 1998

[54] GAS CONCENTRATION SENSOR

[75] Inventors: James D. Seefeldt, DeForest; Michael F. Mattes, Janesville, both of Wis.

[73] Assignee: SSI Technologies, Inc., Janesville, Wis.

[21] Appl. No.: 624,668

[22] Filed: Apr. 2, 1996

[51] Int. Cl.$^6$ .................................................. G01N 7/00
[52] U.S. Cl. ........................................ 73/23.2; 73/31.04
[58] Field of Search ............................. 73/23.2, 24.01, 73/24.04, 24.05, 24.06, 25.04, 30.02, 31.04, 31.05

[56] References Cited

U.S. PATENT DOCUMENTS

| | | |
|---|---|---|
| 2,484,207 | 10/1949 | Criner et al. . |
| 2,638,784 | 5/1953 | Cesaro et al. . |
| 3,510,696 | 5/1970 | Bargen et al. . |
| 3,665,756 | 5/1972 | Russell . |
| 3,817,085 | 6/1974 | Stubbs . |
| 4,305,724 | 12/1981 | Micko . |
| 4,327,350 | 4/1982 | Erichsen . |
| 4,351,181 | 9/1982 | Currans . |
| 4,352,087 | 9/1982 | Wittmaier . |
| 4,368,575 | 1/1983 | Erichsen et al. . |
| 4,393,686 | 7/1983 | Fengler . |
| 4,461,166 | 7/1984 | Gatten et al. ................ 73/25.04 X |
| 4,480,252 | 10/1984 | Buonavita . |
| 4,498,330 | 2/1985 | Hosoya . |
| 4,520,653 | 6/1985 | Kaiser . |
| 4,545,255 | 10/1985 | Pugnaire . |
| 4,572,900 | 2/1986 | Wohltjen . |
| 4,766,763 | 8/1988 | Kurtz . |
| 4,809,810 | 3/1989 | Elfman et al. ................ 73/31.04 X |
| 4,854,155 | 8/1989 | Poli . |
| 4,858,461 | 8/1989 | Steinle et al. . |
| 5,150,603 | 9/1992 | Boenning et al. . |
| 5,179,523 | 1/1993 | Johnson . |
| 5,410,908 | 5/1995 | Erichsen . |
| 5,428,985 | 7/1995 | Kurtz et al. ................ 73/31.04 X |
| 5,507,171 | 4/1996 | Mattes et al. .................. 73/4 R |

FOREIGN PATENT DOCUMENTS

| | | | |
|---|---|---|---|
| 285454 | 11/1988 | Japan ................ | 73/23.2 |
| 307636 | 12/1989 | Japan ................ | 73/23.2 |
| 249063 | 9/1993 | Japan ................ | 73/30.02 |

*Primary Examiner*—Hezron E. Williams
*Assistant Examiner*—Daniel S. Larkin
*Attorney, Agent, or Firm*—Michael Best & Friedrich

[57] ABSTRACT

A gas concentration sensor for use in a closed container having a constant volume and gas within the container, wherein the gas has a known pressure at a given temperature. The sensor includes a pressure sensing device disposed within the container, wherein the pressure sensing device generates a first electrical signal functionally related to the gas pressure within the container. The sensor also includes an electronic circuit connected to the pressure sensing device which amplifies the first electrical signal and produces a second electrical signal functionally related to the gas concentration within the volume at any temperature.

15 Claims, 2 Drawing Sheets

GAS CONCENTRATION SENSOR

BACKGROUND OF THE INVENTION

The present invention relates to sensors, and in particular, to a method and apparatus for measuring gas concentration utilizing a pressure sensing device.

In the past, various semiconductor materials have been used as the sensing element to measure the concentration of different gases. For example, the electrical resistance of certain semiconductors, such as tin dioxide, varies in accordance with changes in the concentration of certain gases.

Another type of gas concentration sensor utilizes a pair of gas filled cylinders. The concentration of the gas in one cylinder is referenced against the concentration of the gas in the other and if the pressure in one container drops below that of the other container, a switch is opened or closed to indicate a change in gas concentration.

SUMMARY OF THE INVENTION

One disadvantage of using various semiconductor materials to directly measure gas concentration is that the semiconductor sensing element must be sensitive to the specific gas whose concentration is to be measured. Other disadvantages attendant to the use of such devices include their nonlinearity and low sensitivity. Further, additional circuitry is often required for temperature compensation, as is illustrated in U.S. Pat. No. 4,498,330, entitled "Gas Detecting and Monitoring Device", issued to Toshiro Hosoya.

A major disadvantage of utilizing two cylinders as a gas concentration sensor is that the device is relatively large in size, typically greater than one cubic inch.

Accordingly, it is an object of the present invention to measure gas concentration in a closed or constant volume container by utilizing a pressure sensing device having a known response to temperature in combination with an electronic circuit having a temperature response selected such that the output signal from the resultant combination of sensing device and circuit is functionally related to the gas concentration in the container and such that the gas concentration sensor is compensated for variations in temperature.

In one embodiment, the pressure sensing device includes piezoresistive elements arranged in a Wheatstone bridge configuration, with the piezoresistive elements and electronic circuit integrated on a single semiconductor chip. The electronic circuit includes a gain circuit and a comparator circuit. The temperature responses of designated resistors in the gain and comparator circuits are selected by varying the implant level of various dopants during the manufacturing process with the result that the gas concentration sensor can accurately detect gas concentration changes in the container regardless of variations in the temperature of the gas in the container.

It is a principal advantage of the invention to provide a gas concentration sensor that is temperature compensated. Other advantages of the invention include providing a gas concentration sensor that is small in size, reliable, easy to manufacture, and low in cost. Additionally, because various electronic circuits may be utilized in conjunction with the pressure sensing device, a variety of signal outputs are possible for connection to different electronic control units.

Other features and advantages of the invention are set forth in the following detailed description and claims.

Figure 1:
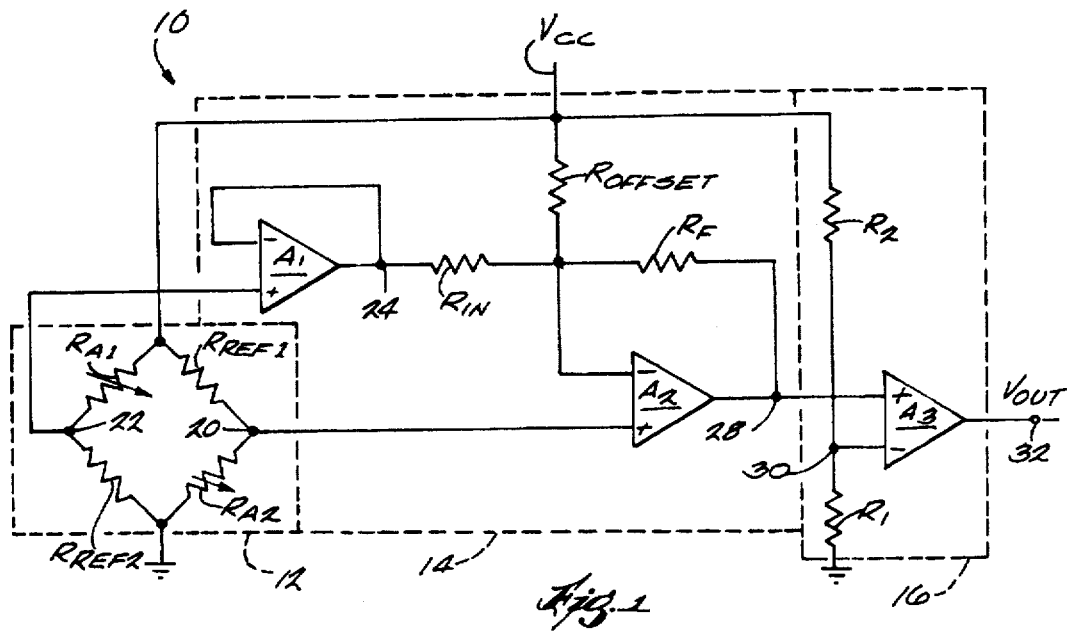
FIG. 1 is a schematic circuit diagram of a gas concentration sensor embodying the invention.

Before one embodiment of the invention is explained in detail, it is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting.

DETAILED DESCRIPTION OF THE PREFERRED EMBODIMENT

Illustrated in FIG. 1 of the drawings is a gas concentration sensor 10. The gas concentration sensor includes a pressure sensing device 12, a gain circuit 14, and a comparator circuit 16.

Figure 3:
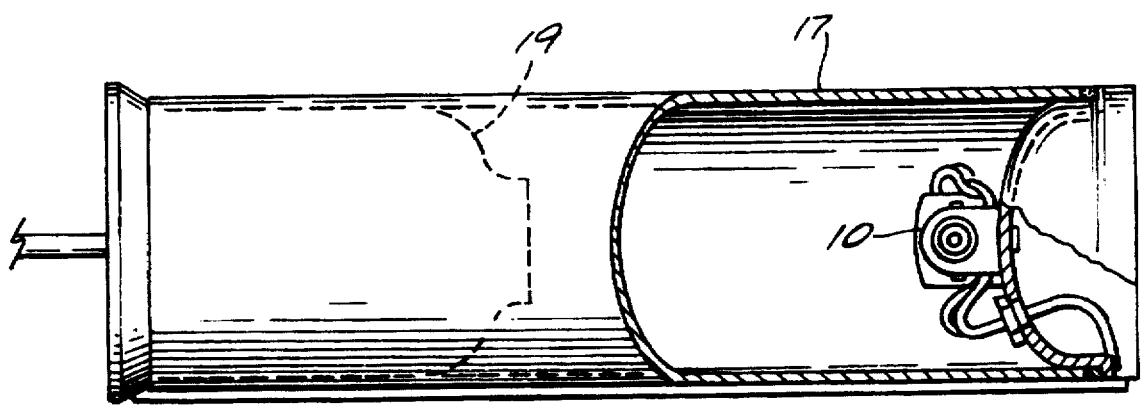
FIG. 3 is a diagram of an air bag inflating canister in which the gas concentration sensor is used.

Gas concentration sensor 10 is preferably connected to or mounted within an enclosed, constant volume container so as to be able to directly measure the gas pressure in the container. For example, sensor could be used in conjunction with an air bag inflating canister 17, as illustrated in FIG. 3, to insure that the concentration of gas within the canister is sufficient to properly inflate an air bag when necessary. Canister 17 is part of a passenger air bag inflator which also includes initiator 19, as is well known in the art.

Referring back to FIG. 1, the pressure sensing device 12 is a resistor bridge network that may be a half-bridge resistor network, a full-bridge resistor network or any other combination of silicon or polysilicon resistors that have an impedance that varies with pressure applied to the device. The pressure sensing device could also be a single resistor in a network that causes a varying voltage to develop across the resistor and causes the voltage to vary in response to changes in ambient pressure.

As shown in FIG. 1, pressure sensing device 12 includes four resistors, $R_{REF1}$, $R_{REF2}$, $R_{A1}$, and $R_{A2}$, arranged in a standard half-active Wheatstone bridge configuration. Resistors $R_{A1}$ and $R_{A2}$ are piezoresistive elements each formed on a polysilicon diaphragm so that pressure exerted on the diaphragm causes movement of the diaphragm and a corresponding change in the resistance of resistors $R_{A1}$ and $R_{A2}$. Preferably, the resistance of resistors $R_{A1}$ and $R_{A2}$ linearly increases with an increase in pressure exerted on the diaphragm. Resistors $R_{REF1}$ and $R_{REF2}$ are inactive with respect to pressure, i.e., the resistance values of $R_{REF1}$ and $R_{REF2}$ do not change with changes in pressure. Although any appropriate semiconductor pressure sensing device can be used, the pressure sensing device of the preferred embodiment is shown and described in U.S. Pat. Nos. 4,744,863, 4,853,669, and 4,996,082; which are incorporated herein by reference.

The Wheatstone bridge is excited by a constant voltage source $V_{CC}$ connected between resistors $R_{A1}$ and $R_{REF1}$ with a common or ground reference connected between resistors $R_{REF2}$ and $R_{A2}$. Pressure sensing device 12 also includes voltages $V_{BR1}$ and $V_{BR2}$ at bridge nodes 20 and 22 respectively for transmitting a differential voltage output indicative of the pressure to which the pressure sensing device is exposed.

Gain circuit 14 includes operational amplifiers A1 and A2 as well as resistors $R_{IN}$, $R_F$, and $R_{OFFSET}$. Bridge node 22 is connected to the positive (non-inverting) input terminal of operational amplifier A1. Operational amplifier A1 has voltage $V_A$ at output node 24 and is connected in the voltage follower mode such that voltage $V_A$ follows voltage $V_{BR2}$ at the positive input terminal of A1. Output node 24 is connected to the negative (inverting) input terminal of A2 through resistor $R_{IN}$. Bridge node 20 is connected to the positive (non-inverting) input terminal of operational amplifier A2.

Operational amplifier A2 is connected in the differential mode so as to amplify the voltage difference between voltages $V_{BR1}$ and $V_{BR2}$. Resistor $R_F$ is connected between the negative (inverting) input terminal of A2 and output node 28 of operational amplifier A2. Resistor $R_{OFFSET}$ is connected between voltage source $V_{CC}$ and the negative input terminal of A2. The following equation represents voltage $V_G$ at output node 28 of differential amplifier A2:

$$V_G = (R_F/R_{IN}) \times (V_{BR1} - V_{BR2}) + (R_F/R_{OFFSET}) \times (V_{BR1} - V_{CC}) + V_{BR1} \quad \text{Equation (1)}$$

Output node 28 is connected to the comparator circuit 16. The comparator circuit 16 includes operational amplifier A3 and resistors $R_1$ and $R_2$. Specifically, node 28 is connected to the positive (non-inverting) input terminal of operational amplifier A3. The negative (inverting) input terminal of operational amplifier A3 is connected to voltage source $V_{CC}$ through resistor $R_2$ and to ground through resistor $R_1$ to generate a reference voltage $V_{REF}$ at node 30 as set forth below:

$$V_{REF} = [R_1/(R_1+R_2)] \times V_{CC} \quad \text{Equation (2)}$$

Voltage $V_{OUT}$ at output node 32 of operational amplifier A3 is equal to a logical "1" when voltage $V_G$ is greater than voltage $V_{REF}$, and is equal to a logical "0" when voltage $V_G$ is less than voltage $V_{REF}$.

In the preferred embodiment, resistors $R_{IN}$, $R_{OFFSET}$, $R_F$, $R_1$, and $R_2$ are formed of a thin film of polysilicon on the same substrate as the pressure sensing device 12 and operational amplifiers A1, A2, and A3 and therefore are exposed to the same ambient temperature as the pressure sensing device 12. The resistance of these resistors varies in response to fluctuations in temperature. The degree to which the resistance of the resistors varies in response to fluctuations in temperature is directly related to the temperature coefficient of the material forming the resistors. For example, the polysilicon resistors may be doped with selected concentrations of impurities such as boron, phosphorus, arsenic or antimony, as is well known in the art. The type and amount of dopant for the selected resistors is chosen so as to establish a predetermined temperature response for the gain circuit 14 and comparator circuit 16, as more fully explained below.

In general operation, the gas concentration sensor 10 is placed in a closed volume container such that the pressure of the gas within the container is sensed by the pressure sensing device 12, and such that all components are simultaneously exposed to the same ambient temperature. The gas concentration sensor 10 utilizes the pressure sensing device 12 to sense the pressure of the gas. Thus, the actual physical property sensed is pressure, but the temperature response of the gain circuit 14 and the comparator circuit 16 are selected such that the output of the sensor, $V_{OUT}$, is an electronic signal indicative of gas concentration.

As previously mentioned, sensor 10 could be used in conjunction with an air bag inflating canister to insure that the concentration of gas within the canister is sufficient to properly inflate an air bag when necessary. The output of the sensor $V_{OUT}$ is either a logical "1", used to indicate that the canister contains a sufficient amount of gas, or a logical "0", used to indicate that the amount of gas in the canister is insufficient to properly inflate the air bag.

In order to compensate for changes in absolute gas pressure resulting from changes in the temperature of gas in the container, the temperature response of the gain circuit (TRG) and the temperature response of the comparator circuit (TRC) are selected such that when combined with the temperature response of bridge sensitivity (TRBS) and the temperature response of the gas pressure (TRGP), the voltage $V_{OUT}$ will be a signal indicative of gas concentration. Thus, $V_{OUT}$ will remain at a logical "1" if the gas concentration remains constant, even with temperature variations. Additionally, the voltage $V_{OUT}$ will switch to a logical "0" when the gas concentration decreases below a predetermined concentration.

By utilizing units of parts per million per degree centigrade (ppm/°C.) for the temperature response, the voltage $V_{OUT}$ is a measure of gas concentration if Equation (3) below is approximately true:

$$\text{TRGP} + \text{TRBS} + \text{TRG} + \text{TRC} = 0 \quad \text{Equation (3)}$$

To calculate the temperature response of gas pressure (TRGP) it is necessary to use the Ideal Gas Law as set forth in Equation (4) below:

$$PV = nRT \quad \text{Equation (4)}$$

where:

P=pressure of the gas

V=volume n=number of moles of gas

R=universal gas constant

T=Temperature in Kelvin.

In a closed volume system, V, n, and R are constant and according to Equation (4), it follows that:

$$P = kT \quad \text{Equation (5)}$$

where k is a proportionality constant representing the temperature response of gas pressure for a specific pressure and temperature. In simple terms, if the gas concentration remains constant, as the temperature increases, the gas pressure also increases, and as the temperature decreases, the gas pressure decreases in a linear manner. If P=2000 PSI at T=25° C., the TRGP is calculated to be approximately 3350 ppm/°C.

The temperature response of bridge sensitivity (TRBS) is a characteristic of the specific piezoresistors of the pressure sensing device and may be empirically determined. In simple terms, it has been determined that the sensitivity of the bridge output voltage to pressure (e.g. volts/psi) will decrease as the temperature increases. In the preferred embodiment, the temperature response of bridge sensitivity is approximately −1500 ppm/°C.

Using Equation (3), the temperature response required from the gain circuit and comparator circuit is approximately −(3350−1500)=−1850 ppm/°C. To calculate the temperature response of the gain circuit, it is necessary to quantify the temperature response of the resistors $R_{IN}$, $R_F$, and $R_{OFFSET}$ as follows:

$$R_{IN}(T)=R_{IN0}[1+\alpha_{IN}(T-T_o)] \qquad \text{Equation (6)}$$

where:

$R_{IN0}$=Resistance of $R_{IN}$ at reference temperature (25° C.)
$\alpha_{IN}$=Temperature coefficient of
T=Operating temperature
$T_o$=Reference temperature (25° C.) Similarly, $$R_F(T)=R_{F0}[1+\alpha_F(T-T_o)] \qquad \text{Equation (7)}$$

$$R_{OFFSET}(T)=R_{OFFSET0}[1+\alpha_{OFFSET}(T-T_o)] \qquad \text{Equation (8)}$$

In the preferred embodiment, at a given reference temperature, the resistance of $R_{OFFSET}$ is substantially equal to the resistance of the feedback resistor $R_F$, and the polysilicon for each is doped using the same implant concentration so that the temperature coefficient of $R_{OFFSET}$ is substantially equal to the temperature coefficient of $R_F(\alpha_F=\alpha_{OFFSET})$. Substituting the temperature dependent values of $R_F$, $R_{OFFSET}$ and $R_{IN}$ into Equation (1) results in the following equation for the temperature response of the gain circuit:

$$V_G = \frac{R_{F0}[1+\alpha_F(T-T_o)]}{R_{IN0}[1+\alpha_{IN}(T-T_o)]}(V_{BR1}-V_{BR2}) + \frac{R_{F0}}{R_{OFFSET0}}(V_{BR1}-V_{CC})+V_{BR1} \qquad \text{Equation (9)}$$

The last two terms of Equation (9) are not temperature dependent. Therefore, the temperature response of the gain circuit is a function of the temperature coefficients $\alpha_F$ and $\alpha_{IN}$ of the resistors $R_F$ and $R_{IN}$, respectively. The temperature coefficients $\alpha_F$ and $\alpha_{IN}$ may be expressed in parts per million/°C. and their values are a function of the particular material used to form $R_F$ and $R_{IN}$. As previously discussed, the materials comprising resistors $R_F$ and $R_{IN}$ may be precisely selected to vary the differential gain in response to variations in temperature thereby producing an output that, for a given input, varies in a known way in response to temperature variations or is substantially constant in response to temperature variations.

By implanting resistors $R_{IN}$, $R_F$, and $R_{OFFSET}$ so that the resistivity of input resistor $R_{IN}$ decreases and the resistivities of feedback resistor $R_F$ and offset resistor $R_{OFFSET}$ increase when the gas concentration sensor is subjected to an increase in temperature, the gain circuit has a negative temperature response. For example, doping $R_{IN}$ with phosphorus at approximately $2.2\times10^{15}$ cm$^{-2}$, and doping $R_F$ and $R_{OFFSET}$ with phosphorus at approximately $1.8\times10^{16}$ cm$^{-2}$, results in a TRG of approximately $-1500$ ppm/°C. Other dopants such as boron, arsenic or antimony may be appropriate, depending on the temperature response required and such dopants can be used in varying concentrations depending upon the application.

According to Equation (3), the required temperature response for the comparator circuit is approximately $-350$ ppm/°C. Resistors $R_1$ and $R_2$ can be expressed as follows:

$$R_1(T)=R_{10}[1+\alpha_1(T-T_o)] \qquad \text{Equation (10)}$$

$$R_2(T)=R_{20}[1+\alpha_2(T-T_o)] \qquad \text{Equation (11)}$$

Substituting Equations (10) and (11) into Equation (2):

$$\frac{V_{REF}}{V_{CC}} = \frac{R_{10}(1+\alpha_1(T-T_o))}{R_{10}+R_{20}+[(\alpha_1 R_{10})+(\alpha_2 R_{20})](T-T_o)} \equiv$$

$$\frac{R_{10}}{R_{10}+R_{20}}\left[1+\left(\alpha_1-\frac{\alpha_1 R_{10}+\alpha_2 R_{20}}{R_{10}+R_{20}}\right)(T-T_o)\right]$$

$$V_{REF} = V_{REF0}[1+\alpha_{REF}(T-T_o)]$$

$$\left(\alpha_1-\frac{\alpha_1 R_{10}+\alpha_2 R_{20}}{R_{10}+R_{20}}\right) \equiv -350 \text{ ppm/}\cdot C = \alpha_{REF}$$

The last equation may then be solved for $\alpha_1$ and $\alpha_2$. Appropriate doping levels may then be selected for $R_1$ and $R_2$ to achieve the required temperature response for the comparator circuit.

A description of selection of components for the gas concentration sensor will now be provided. For a given pressure and reference temperature, for example, 2000 psi at 25° C., the pressure sensing device 12 should operate somewhere in the middle of its range. This is because (assuming the gas concentration remains constant) as temperature increases, the gas pressure will increase and as the temperature decreases, the gas pressure will decrease, and pressure sensing device 12 must have a useful output for the changing pressure over the required temperature range of operation.

For a given pressure and reference temperature, voltage $V_G$ will have a specific value depending on the gain of circuit 14. Selection of reference temperature resistance values for $R_F$, $R_{IN}$, and $R_{OFFSET}$ is within the knowledge of one skilled in the art. Voltage $V_{REF}$ at node 30 is set to be indicative of a gas concentration setpoint below which the output of comparator A3 will switch to a logical "0". Selection of this voltage is dependent on the tolerance desired.

Figure 2:
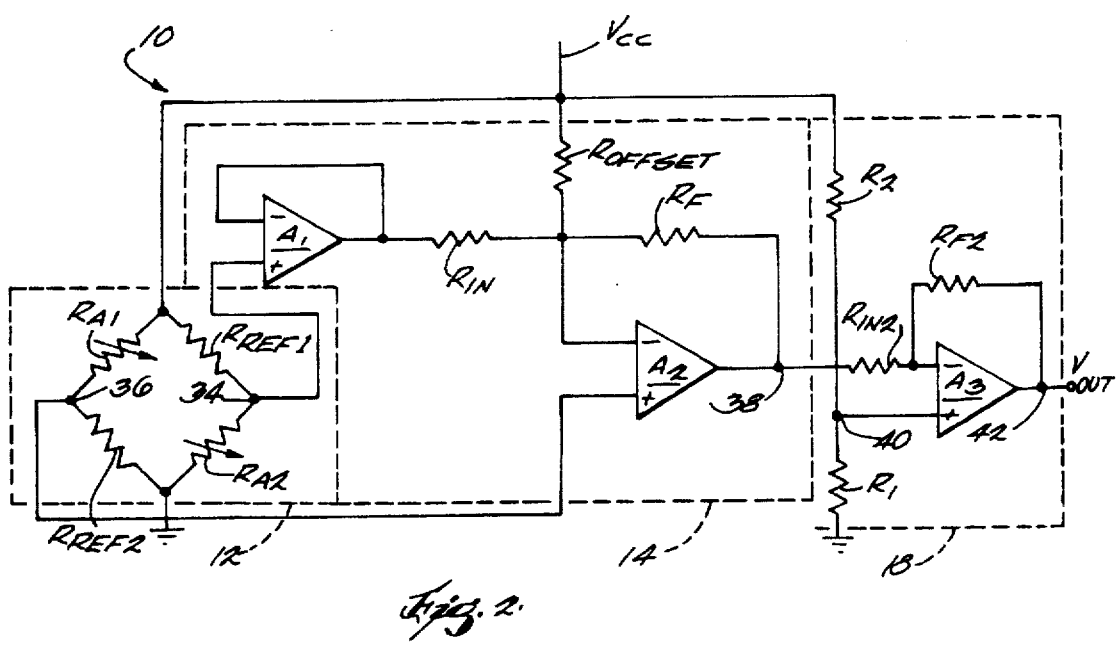
FIG. 2 is a schematic circuit diagram of a gas concentration sensor that is a second embodiment of the invention.

FIG. 2 illustrates a second embodiment of the gas concentration sensor. The gas concentration sensor includes a pressure sensing device 12, a first gain circuit 14 and a second gain circuit 18. The pressure sensing device 12 of FIG. 2 is the same as that previously described with respect to FIG. 1 with like reference numerals and characters designating identical or corresponding elements.

The first gain circuit of FIG. 2 is the same as the gain circuit previously described with respect to FIG. 1. However, bridge nodes 34 and 36 of pressure sensing device 12 in FIG. 2, having voltages $V_{BR1}$ and $V_{BR2}$ respectively, are reversed from the way nodes 20 and 22 are connected to the gain circuit in FIG. 1. The following equation represents voltage $V_G$ at node 38 of differential amplifier A2 in FIG. 2:

$$V_G=(R_F/R_{IN})\times(V_{BR2}-V_{BR1})+(R_F/R_{OFFSET})\times(V_{BR2}-V_{CC})+V_{BR2}$$

The second gain circuit 18 includes operational amplifier A3 and resistors $R_1$, $R_2$, $R_{IN2}$, and $R_{F2}$. Specifically, node 38 of the first gain circuit is connected to the negative input terminal of operational amplifier A3 through resistor $R_{IN2}$. Output node 42 of operational amplifier A3 is connected to its negative input terminal through resistor $R_{F2}$. The positive input terminal of operational amplifier A3 is connected to voltage source $V_{CC}$ through resistor $R_2$ and to ground through resistor $R_1$ to generate a reference voltage $V_{REF}$ at node 40, where:

$$V_{REF}=[R_1/(R_1+R_2)]\times V_{CC} \qquad \text{Equation (12)}$$

If resistors $R_1$ and $R_2$ are doped with the same concentrations of dopant, voltage $V_{REF}$ will remain essentially constant (assuming that the gas concnetration is constant) regardless of temperature changes.

The voltage at the output of the operational amplifier A3 at node 42 is defined by:

$$V_{OUT}=(R_{F2}/R_{IN2})(V_{REF}-V_G)+V_{REF} \quad \text{Equation (13)}$$

The output voltage $V_{OUT}$ differs from the output generated by the circuit of FIG. 1 in that $V_{OUT}$ is an analog voltage output which provides a real time indication of the gas concentration in the container. The sensor of FIG. 2 operates in a similar manner to the sensor of FIG. 1. The temperature response of the first gain circuit of FIG. 2 is the same as that of the gain circuit of FIG. 1. The desired temperature response for the second gain circuit 18 of FIG. 2 is 350 ppm/°C. From Equation (13), the temperature response of $V_{OUT}$ is dependent on $R_{F2}$ and $R_{IN2}$. Resistors $R_{F2}$ and $R_{IN2}$ can be expressed as follows:

$$R_{F2}(T)=R_{F20}[1+\propto_{F2}(T-T_o)] \quad \text{Equation (14)}$$

$$R_{IN2}(T)=R_{IN20}[1+\propto_{IN2}(T-T_o)] \quad \text{Equation (15)}$$

Equations (14) and (15) are substituted into Equation (13) and Equation (13) is solved for $\propto_{F2}$ and $\propto_{IN2}$. Appropriate doping levels to achieve the desired temperature response are then selected for resistors $R_{F2}$ and $R_{IN2}$.

What we claim is:

1. A gas concentration sensor for use in a closed container having a constant volume and gas within said container, the gas having a known pressure at a given temperature, the sensor comprising:

a pressure sensing device disposed within said container, said pressure sensing device generating a first electrical signal functionally related to the gas pressure within said container; and an electronic circuit connected to said pressure sensing device, said electronic circuit including an operational amplifier and a plurality of doped polysilicon resistors for determining the gain of said operational amplifier, wherein at least one of said doped polysilicon resistors has an impedance that varies with varying temperature such that the gain of said operational amplifier varies in a predetermined way with varying temperature, and wherein said electronic circuit amplifies said first electrical signal, and produces a second electrical signal functionally related to the gas concentration within the volume at any temperature.

2. The gas concentration sensor of claim 1 wherein said pressure sensing device includes piezoresistors arranged in a Wheatstone bridge configuration.

3. The gas concentration sensor of claim 2 wherein said Wheatstone bridge is excited by a constant voltage source.

4. The gas concentration sensor of claim 1 wherein said electronic circuit includes a gain circuit and a comparator circuit.

5. The gas concentration sensor of claim 4 wherein said gain circuit includes first and second operational amplifiers.

6. The gas concentration sensor of claim 1 further comprising a comparator circuit connected to said electronic circuit, said comparator circuit generating an output indicative, at any temperature, of a change in the gas concentration within said container.

7. The gas concentration sensor of claim 1 wherein one of said doped polysilicon resistors is a feedback resistor doped with phosphorus at approximately $1.8 \times 10^{16}$ cm$^{-2}$ and another of said doped polysilicon resistors is an input resistor doped with phosphorus at approximately $2.2 \times 10^{15}$ cm$^{-2}$ such that the gain of said amplifier varies in inverse proportion to temperature variations.

8. A gas concentration sensor for use in a closed container having a constant volume and gas within the container, the gas having a known pressure at a given temperature and the gas pressure having a known temperature response, said gas concentration sensor comprising:

a pressure sensing device disposed within said container, said pressure sensing device generating a first electrical signal functionally related to the gas pressure within the container, said first electrical signal having a known non-zero pressure sensitivity temperature response; and an electronic circuit connected to said pressure sensing device, said electronic circuit including an operational amplifier and a plurality of doped polysilicon resistors for determining the gain of said operational amplifier, wherein at least one of said doped polysilicon resistors has an impedance that varies with varying temperature such that the gain of said operational amplifier varies in a predetermined way with varying temperature, and wherein said electronic circuit amplifies said first electrical signal, and produces a second electrical signal, said electronic circuit having a known temperature response selected such that when combined with the gas pressure temperature response and the pressure sensitivity temperature response, said second electrical signal is functionally related to the gas concentration within said container.

9. The gas concentration sensor of claim 8 wherein said pressure sensing device includes piezoresistors arranged in a Wheatstone bridge configuration.

10. The gas concentration sensor of claim 9 wherein said Wheatstone bridge is excited by a constant voltage source.

11. The gas concentration sensor of claim 9 wherein said electronic circuit includes a gain circuit and a comparator circuit.

12. The gas concentration sensor of claim 11 wherein said gain circuit includes first and second operational amplifiers.

13. The gas concentration sensor of claim 8 further comprising a comparator circuit connected to said electronic circuit, said comparator circuit generating an output indicative, at any temperature, of a change in the gas concentration within said container.

14. The gas concentration sensor of claim 8 wherein one of said doped polysilicon resistors is a feedback resistor doped with phosphorus at approximately $1.8 \times 10^{16}$ cm$^{-2}$ and another of said doped polysilicon resistors is an input resistor doped with phosphorus at approximately $2.2 \times 10^{15}$ cm$^{-2}$, such that the gain of said amplifier varies in inverse proportion to temperature variations.

15. A method of measuring the gas concentration in a closed container having a constant volume and gas within said container, the gas having a known pressure at a given temperature, said method comprising:

providing a pressure sensing device in said container, generating a first electrical signal from the pressure sensing device, said first electrical signal functionally related to the gas pressure within said container;

providing an operational amplifier including a plurality of doped polysilicon resistors for determining the gain of the operational amplifier, wherein at least one of the doped polysilicon resistors has an impedance that varies with varying temperature such that the gain of the operational amplifier varies in a predetermined way with varying temperature; and amplifying said first electrical signal with the operational amplifier to produce a second electrical signal functionally related to the gas concentration within the volume at any temperature.

* * * * *